United States Patent [19]

Ray et al.

[11] Patent Number: 5,000,163
[45] Date of Patent: Mar. 19, 1991

[54] RETRACTION DEVICE

[75] Inventors: Charles D. Ray, Wayzata; Duane J. Zythkovicz, Minneapolis, both of Minn.

[73] Assignee: Surgical Dynamics, Inc., Alameda, Calif.

[21] Appl. No.: 374,911

[22] Filed: Jul. 3, 1989

Related U.S. Application Data

[60] Division of Ser. No. 158,908, Feb. 22, 1988, abandoned, which is a continuation-in-part of Ser. No. 66,147, Jun. 25, 1987, Pat. No. 4,805,599.

[51] Int. Cl.$^5$ .............................................. A61B 17/02
[52] U.S. Cl. .................................. 128/20; 403/131; 24/490
[58] Field of Search ............... 128/20, 17; 269/328; 24/512, 489, 440, 442, 498, 516, 534, 544; 403/DIG. 9, 131, 385, 400

[56] References Cited

U.S. PATENT DOCUMENTS

| | | | |
|---|---|---|---|
| 2,496,645 | 2/1950 | Unwih | 403/385 |
| 2,670,732 | 3/1954 | Nelson | 128/20 |
| 3,039,161 | 6/1962 | Gagmon | 24/490 |
| 3,196,865 | 7/1975 | Rose | 128/20 |
| 4,010,741 | 3/1977 | Gauthier | 128/20 |
| 4,380,999 | 4/1983 | Healy | 128/20 |
| 4,487,523 | 12/1984 | Monroe | 403/385 |

Primary Examiner—Edward M. Coven
Assistant Examiner—Mark S. Graham
Attorney, Agent, or Firm—Fliesler, Dubb, Meyer & Lovejoy

[57] ABSTRACT

During back surgery, a surgeon can, with one hand, apply traction against tissue in a surgical wound by using a retraction device that includes an upstanding post and a surgical retractor, the handle of which is formed with ratchet teeth for securing the retractor to the post against elastic recoil of the retracted tissue. The post preferably is integral with a slip-lock which can be slidably mounted on a rectangular rail of a framework that extends above the patient. The slip-lock includes a floating jaw that is loosely pinned to a slide and becomes releasably locked to the rail when the elastic recoil of retracted tissue pulls on the post. Because the retraction device holds the tissue precisely in the position to which it is set by the surgeon, the hazards involved in using assistants to hold retractors are avoided.

9 Claims, 4 Drawing Sheets

RETRACTION DEVICE

CROSS-REFERENCE TO COPENDING APPLICATION

This is a division of application Ser. No. 07/158,908, abandoned filed Feb. 22, 1988, which in turn was a continuation-in-part of application Ser. No. 07/066,147, filed June 25, 1987 (now U.S. Pat. No. 4,805,599) issued Feb. 21, 1989.

BACKGROUND OF THE INVENTION

1. Field of the Invention

The invention relates to a device for retracting tissue at a surgical wound. The retraction device of the invention is particularly useful during back surgery in conjunction with a kneeling attachment including a platform on which a patient kneels with the torso positioned over one end of an operating table while the buttocks rest against a buttocks support. The novel retraction device can also be used during back surgery on a prone, face-down patient.

2. Description of Related Art

U.S. Pat. No. 4,254,763 (McCready et al.) reports that in "surgical operations on the chest or abdomen, it is customary to employ a retraction apparatus. Most, if not all, versions of the retraction apparatus are attached directly to the operating room table by means of affixation to a rail which is provided along each side of the table. Whether by connection to one or both rails, the retraction apparatus generally provides a framework extending over the region of the patient in which the operation is to be performed. One or more retractor blades are attached to the framework, and these blades are positioned in the incision and serve to hold back tissue, organs, and the like so that the surgeon may operate on the intended area" (col. 1, lines 11-27). While the McCready framework includes a ring-like frame from which retractors are suspended, a number of patents show rectangular frames. See, for example, U.S. Pat. No. 3,522,799 (Gauthier), No. 3,221,743 (Thompson et al.). No. 3,572,326 (Jensen), and No. 4,355,631 (LeVahn). Other U.S. patents showing ring-like frames include No. 2,586,488 (Smith), 2,594,086 (Smith), and 3,040,739 (Grieshaber). A frame of different shape is shown in U.S. Pat. No. 4,617,916 (LeVahn et al.). The framework of each of these patents is supported by siderails of the operating table, except that we fail to find in Gauthier any mention of support for his framework.

Apparatus like that shown in the LeVahn et al. patent is sold for use in abdominal surgery as the Omni-Tract 3005 Upper Abdominal/Bariatric Retractor System by Minnesota Scientific, Inc., Minneapolis, MN. The Omni-Tract framework includes a "crossbar" that is clamped by one or two posts to one or both rails of an operating table. Universal joints at the top of each of the posts permit the crossbar to be adjusted to the desired height and lateral distance from the surgical wound. Retractors can be mounted on the crossbar using universal clamps which can be swiveled to provide the desired lateral retraction from positions that do not obstruct access to the wound. Such universal clamps involve elaborate sequences to be connected, readjusted or disconnected and thus do not permit quick response to urgent situations.

Because of the far greater force needed to retract the powerful muscles of the back, certain abdominal muscles, and the thoracic cage, the above-discussed frameworks are not said to be useful for such purposes. Furthermore, it is believed that no framework is available that would be suitable for supporting retractors above a surgical wound in the back. Instead of using such a framework, it is quite common in back surgery for a surgical assistant to hold a Hibbs-type retractor in place manually, sometimes for several hours. Not only does this fully occupy the assistant, but there is a danger that the assistant could move the retractor in a hazardous manner, and the danger could be amplified due both to fatigue and to boredom.

When it is desired to attach accessories to an operating table, the most common attachment devices are Clark sockets such as No. 5393 of Orthopedic Systems, Inc., Hayward, CA. The Clark sockets are designed to be clamped to a side rail of the operating table and are so made that all degrees of freedom are loosened at once. Thus, in order to move the patient's buttocks away from or closer to the head of the operating table, a Clark socket is unclamped, also releasing its hold on the accessory. The head-to-foot adjustability of a Clark socket is limited to rather large angular steps. Other sockets and clamps are currently available, but it is believed that they have the same limitations as do Clark sockets.

SUMMARY OF THE INVENTION

The invention provides a retraction device permitting a surgeon, with one hand, to apply and maintain traction against tissue in a surgical wound and to watch the wound continuously while adjusting the direction and extent of the retraction. Because the novel retraction device holds the tissue precisely in the position to which it is set by the surgeon, the hazards involved in using assistants to hold retractors are avoided. Briefly, the retraction device of the invention includes:

a rigid post, means for rigidly mounting the post above the bed of an operating table with the post extending substantially orthogonally to the direction from the post to the wound, a surgical retractor, and means for adjustably securing the retractor to the post against elastic recoil of tissue being retracted by the retractor.

The surgical retractor of the novel retraction device preferably is flat and bent between its blade and handle at an angle of from 45° to 120° so that the handle can extend orthogonally to the post. The means for securing the retractor to the post may include a series of teeth formed in at least one edge of the handle of the retractor, thus providing adjustabilty in that any of the teeth can lock the retractor to the post against the elastic recoil of tissue being retracted. There is no need for teeth in the retractor handle when adjustability is provided by frictionally securing the handle to a T-bar projecting from the post.

The post preferably is fixed to a slip-lock which can be slidably positioned on a substantially horizontal rectangular rail of a framework positioned above the operating table. In a preferred embodiment of the invention, the slip-lock has slide with a flat surface that rests on the rail with another surface that can rest against a side of the rail. A bolt threadably received by the slide loosely pins a C-shaped floating jaw to the slide, and the torque applied to the post by the elastic recoil of tissue being retracted causes the rail to be clamped between the slide and its floating jaw. When the surgeon pivots the post against the tissue recoil, the clamping is released, and the surgeon can easily slide the slip-lock along the rail to a new position, again without taking the eyes away from the wound. Because the post can be moved without releasing the retractor, it is much easier to reposition the patient than it has been in the past.

In another embodiment, the slip-lock has a C-shaped slide, the floating jaw is L-shaped, and only one of its surfaces can be pressed against a side of the rail.

Instead of providing adjustability by means of a series of teeth in a retractor handle, a retractor which has no teeth in its handle can be frictionally secured to a bar projecting laterally from the post, preferably a T-bar so that the retractor can be secured from either side of the post. A slip-lock such as described above becomes locked to the rail whenever the post is manipulated either upwardly or inwardly by the tissue recoil.

Other means for adjustably securing a toothless retractor handle to the post include pinching and clamping devices which preferably are self-actuating. All of the aforementioned means for adjustably securing a retractor afford instant attachment, readjustment and release.

The rail for the slip-lock preferably is at substantially the same height above the operating table as the opening of the surgical wound so that it and the post do not obstruct access to the wound. When the slip-lock is mounted on the rail, the post can extend vertically or can be canted toward the surgical wound, but preferably is at an attitude permitting the handle of an attached surgical retractor to extend approximately orthogonally to the post.

DETAILED DESCRIPTION

The retraction device of the invention is particularly useful in any surgical procedure involving large retraction forces such as in splitting the thoracic cage or in back surgery in conjunction with framework for supporting surgical instruments such as retractors at a surgical wound. In back surgery, a patient may be kneeling on a platform with the chest lying on a thick cushion placed on the surface of an operating table. After the patient has been so positioned and draped with sterile cloths, a sterile framework may be attached through the drapery to the kneeling platform as disclosed in the above-cited parent patent application Ser. No. 07/066,147 (now U.S. Pat. No. 4,805,599). A slip-lock for the rigid post of the novel retraction device preferably rides along either on a rail of that framework or on a rigid crossbar extending between opposed rails of the framework. When the patient is fully prone, the framework can be supported from the siderails of the operating table, or the slip-lock can ride along the siderails without using the framework.

THE DRAWING

The invention will be more easily understood in reference to the drawing, all figures of which are schematic, wherein.

Figure 1:
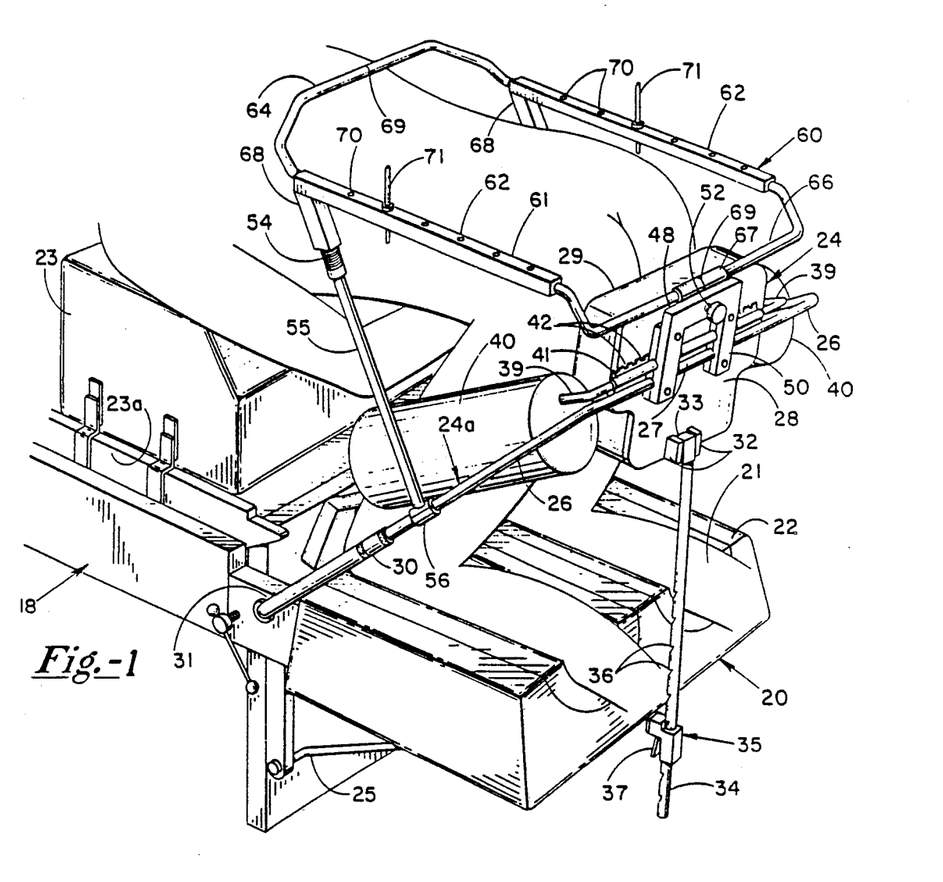
FIG. 1 is a perspective view of a framework mounted on a buttocks support of a kneeling attachment to an operating table, which framework is useful for positioning a retraction device of the invention at a surgical wound.

The framework shown in FIG. 1 includes a unitary, substantially rectangular rigid frame 60 provided by a metal rod 61 that forms a complete rectangle having two relatively long parallel legs or rails 62, the ends of which are interconnected by an arched inboard crossarm 64 and an outboard crossarm 66 which are shorter than the rails. The rigid frame 60 is attached to an operating table 18 having a kneeling attachment 20 permitting a patient 21 to kneel on a platform 22 with the torso positioned over one end of the operting table and resting on a torso cushion 23 which is strapped to the siderails 23a of the operating table 18. The patient's buttocks rest against a buttocks support 24. The platform can either be supported from the floor by a post 25 or can be locked to move up and down with the operating table while the post 25 is retracted as shown in FIG. 1.

The buttocks support 24 includes a metal U-shaped yoke 24a having two arms 26 and a crosspiece 27. Pivotably mounted on the crosspiece is a rigid seatplate 28, on the face of which is a buttocks cushion 29. The arms 26 of the yoke telescope at a friction lock 30 and are pivotably attached at 31 to the inboard end of the platform 22.

Pivotably mounted between two plates 32 bolted to the back of the seatplate 28 is a block 33 that is fixed to the upper end of a metal mast 34, the lower end of which is telescopically connected to the outboard end of the platform 22 by a ratchet assembly 35. Formed in the inner facing surface of the mast 34 are notches 36 into which fit a spring-loaded lever 37 (spring not shown) that can be manually retracted to lower the mast.

Pivotably and slidably positionable at the back of the seatplate 21 is each of a pair of metal L-shaped rods 39. A first arm of each of the rods fits snugly into an off-center bore of a cylindrical thigh-supporting cushion 40. Welded to the second arm of each of the rods is a bracket 41 that is formed with notches 42 into which fits a pin (not shown) protruding from the back of the seatplate 28. When an attendant lifts a thigh-supporting cushion 40, the bracket 41 is moved away from the pin, thus permitting the attendant to slide the second arm of the L-shaped rod 39 in the direction of the crosspiece 27 until its thigh-supporting cushion fits snugly against a patient's thigh, and then to push the cushion downwardly until the pin fits into another notch 42.

At the center of the outboard crossarm 66 of the frame 60 is a hinge 67 having a tang (not seen) that is secured to the back of the seatplate 21 by a bolt 52 to lock the outboard crossarm of the frame 60 to the buttocks support 24.

Extending downwardly from the rails 62 near the ends of the inboard crossarm 64 are internally threaded stubs 68, into each of which is threaded a collar 54 at the end of a shaft 55. The other end of the collar is attached by a split clamp 56 to one of the arms 26 of the U-shaped yoke 24a. The threaded collar permits the frame 60 to be raised or lowered, but the frame should never be lowered to the extent that there is any danger of the inboard crossarm 64 coming into contact with the back of the patient's chest. The inboard crossarm 64 is arched upwardly to minimize any such danger. The metal rod 61 is formed in two pieces that can be disconnected at 69 to fit into a conventional autoclave for sterilization. This disconnectability permits operations to be performed with only one-half of the frame 60 in place.

Although the shafts 55 are supported from the yoke 24a, they preferably are supported from the siderails 23a for increased stability of the frame 60.

The frame 60 should be mounted on the buttocks support 24 after the patient has been covered by surgical drapery. This enables the frame to be removed more quickly should there be an emergency requiring that the patient be turned face-up. Formed in each of the rails 62 is a series of cylindrical openings 70 for receiving posts 71 to which surgical retractors or other instruments can be releasably attached.

Figure 2:
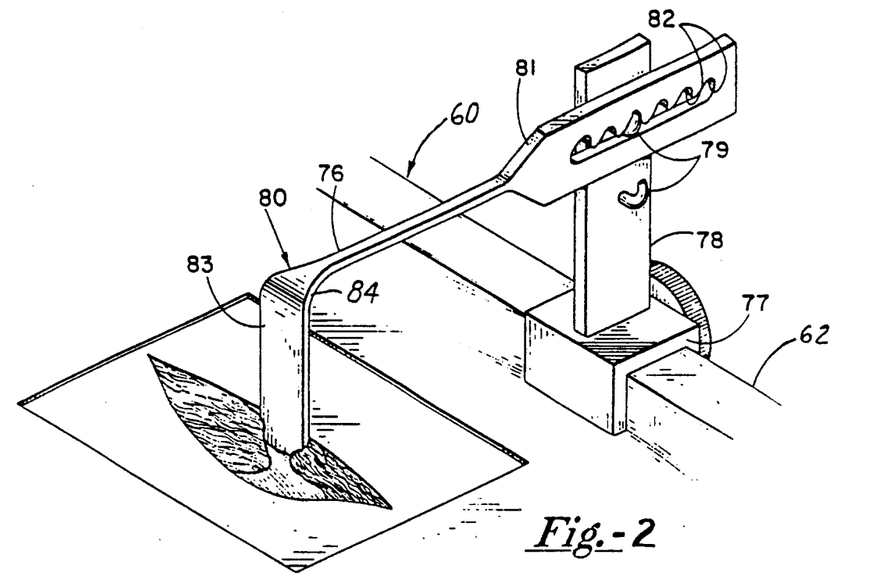
FIG. 2 is a perspective view showing a fragment of the framework of FIG. 1 to which is attached a first preferred embodiment of the retraction device of the invention.

In FIG. 2, locked to a rail 62 of the frame 60 is a slide 77 carrying an upstanding rigid rectangular post 78, from each broad side of which projects two hooks 79. A surgical retractor 80 has an arm or handle 81 formed with a ratchet 82 consisting of a series of teeth that rest on an upper of the hooks 79. The ratchet teeth are held in place by gravity and by elastic recoil of the tissue to maintain the traction applied when the surgeon sets the blade 83 of the retractor in the wound. Both the blade 83 and the handle 81 are flat, and the planes of their flat surfaces intersect at an angle of 90°. A bend 84 in the retractor 80 forms an angle of about 90°.

Figures 3, 8:
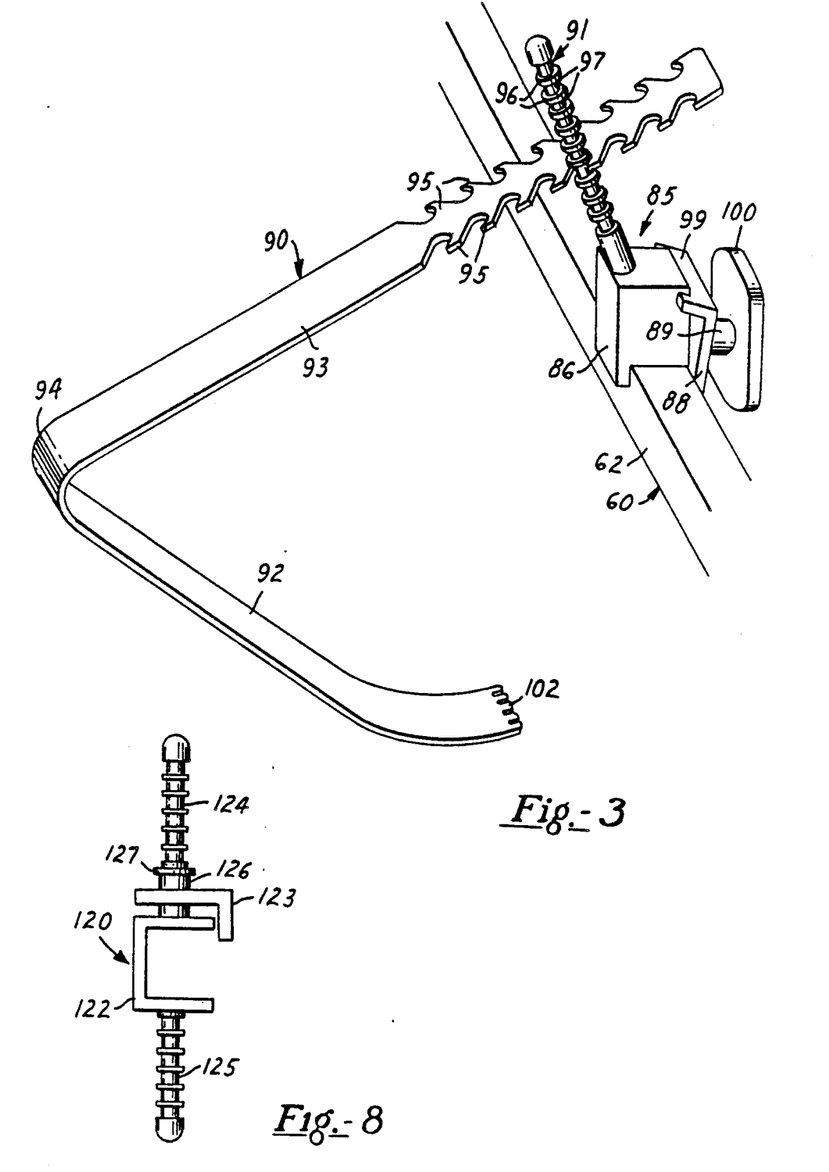
FIG. 3 is a perspective view showing a fragment of the framework of FIG. 1 to which is attached a second preferred embodiment of the retraction device of the invention.
FIG. 8 is an elevation of another retraction device of the invention.

In FIG. 3, mounted on a rail 62 of the frame 60 is a slip-lock 85 consisting of an L-shaped slide 86, a bolt 87 that is threadably received by the slide, a C-shaped jaw 88, and a hemispherical ball 89 that loosely fits over the bolt 87 and into a socket in the C-shaped jaw. Integral with the L-shaped slide 86 is a rigid upstanding post 91 that supports a surgical retractor 90 which (like retractor 80 of FIG. 2) is held by elastic recoil of the tissue to maintain traction applied when the surgeon sets the blade 92 of the retractor in a surgical wound. Both the blade 92 and the handle 93 of the retractor 90 are flat, and a bend 94 between the blade and handle forms an angle of about 70°. Ratchet teeth 95 are formed in each edge of the handle to permit it to be secured to the upstanding post 91 from either side. Because the rail 62 is positioned above the surgical wound, the post 91 is canted to extend toward the wound at an angle of about 25° to the vertical so that it extends substantially orthogonally to the retractor handle 93 after the retractor has been set in the wound.

The post 91 is circular in cross section and is formed with rings 96 spaced by grooves 97, each of a width about 1.5 times the thickness of the retractor handle 93. The rings and grooves keep the retractor from slipping after it has been set. Instead of rings, it would be sufficient to form serrations only in the back face of the post, i.e., the face contacted by retractor teeth 95 when the retractor 90 is set in the wound.

When the bolt 87 is loose and the slip-lock 85 is slipped onto the rail 62, a flat surface of the slide 86 rests on the top of the rail, and the C-shaped jaw 88 (which can be pivoted to its position in FIG. 4) hangs loosely but keeps the slip-lock from falling off the rail. The upper end 99 of the C-shaped jaw is bifurcated to fit loosely around the slide 86, thus preventing the jaw from rotating out of position.

Figure 5:
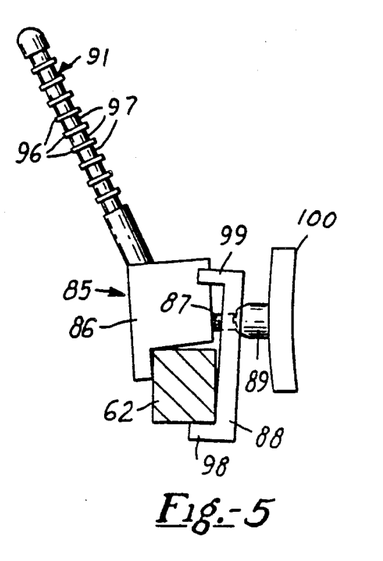
FIG. 5 is an elevation similar to that of FIG. 4 except with the post in a locked position.

After sliding the slip-lock 85 to the desired position along the rail and without tightening the bolt 87, the surgeon can set the blade 92 of the retractor 90 into a surgical wound and fit its ratchet teeth 95 onto the post 91. Elastic recoil of the patient's tissue pivots the post to force the lower extremity of the slide 86 against the inner face of the rail 62, thus forcing the lower end of the C-shaped jaw 88 against the bottom of the rail 62 as shown in FIG. 5. This should prevent further sliding, but to make sure, the bolt 87 can be tightened. When the bolt is left untightened, the surgeon can unlock the slip-lock simply by pushing the post 88 and then can easily slide the slip-lock 85 a short distance along the rail 62 while the retractor 90 remains set in the wound. The slip-lock again becomes locked as soon as the post is released.

Because the slip-lock 85 fits loosely over the rail 62, the rail can be covered with one or more layers of surgical drapery without interfering with the ability to slide the slip-lock along the rail. If preferred, the drapery can extend over the post 91, or it can have a small hole through which the post and the crank 100 of the bolt 86 can protrude. Even if the drapery is caught either between the hemispherical ball 89 and the crank 100 or between the ball and the socket of the slide 86, the bolt still can be tightened or loosened.

The end of the retractor blade 92 is formed with serrations 102 by which it can be stabilized in a surgical wound, but could have other anchoring means such as spikes.

Figure 6:
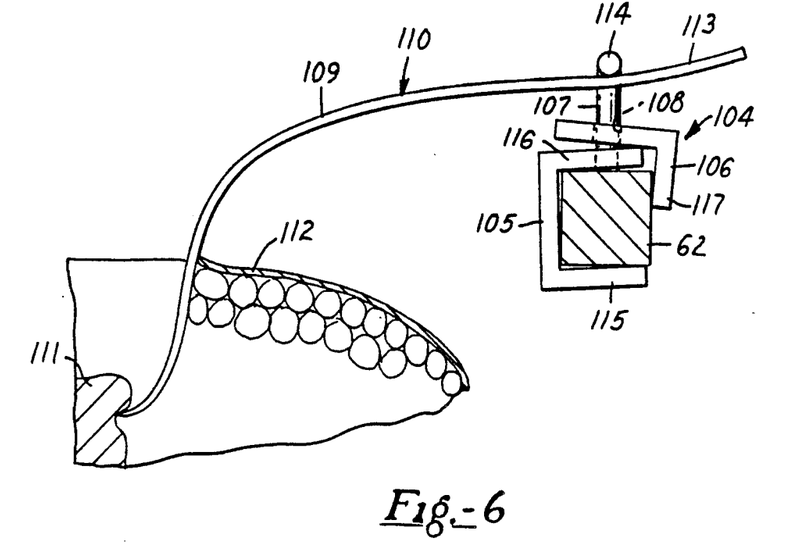
FIG. 6 is an elevation of a third preferred embodiment of the retraction device of the invention.

In FIG. 6, mounted on the rail 62 is a slip-lock 104 having a C-shaped slide 105 and an L-shaped floating jaw 106. Integral with the slide 105 is a rigid upstanding post 107 that loosely fits into a bore 108 through the L-shaped jaw 106. The blade 109 of a surgical retractor 110 has been hooked into bone 111, used to retract a mass of tissue 112, and then secured by placing its handle 113 under one end of a T-bar 114 that is integral with the post 107. The elastic recoil of the tissue exerts a lifting force through the retractor handle against the T-bar to lift the C-shaped slide 105 to the position of FIG. 6. Upon doing so, the extremity of the lower end 115 of the C-shaped slide is pressed against the bottom face of the rail 62, and the upper end 116 of the C-shaped slide is lifted to cause the extremity of the end 117 of the L-shaped jaw 106 to press against the outer face of the rail 62. This locks the slip-lock 104 to remain securely in place until someone pivots the post 107 against the tissue recoil to permit the slip-lock to be moved along the rail until the post is released and thus returned to the locked position of FIG. 6 by the elastic recoil of the retracted tissue.

The same clamping action takes place when the T-bar 114 is rotated either clockwise or counterclockwise, with or without being simultaneously lifted. Hence, the slip-lock 104 and post 107 can replace the slide 77 and post 78 of FIG. 2 and can be used with the retractor 76 by resting its ratchet teeth 82 against either arm of the T-bar.

Figure 7:
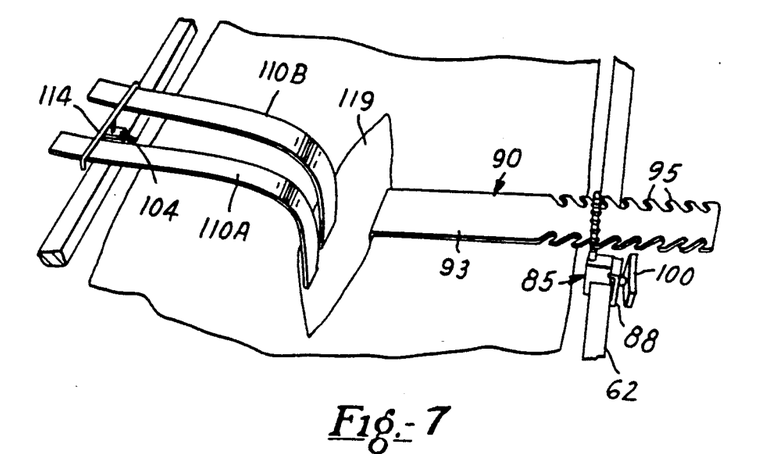
FIG. 7 is a perspective view showing the use of three retraction devices of the invention to keep a surgical wound open.

In FIG. 7, two retractors 110A and 110B are pressing upwardly against the two arms of the T-bar 114 of the slip-lock 104 of FIG. 6 to hold open one side of a surgical wound 119, and the retractor 90 and the slip-lock 85 of FIG. 3 are being used to hold open the other side of the wound.

FIG. 8 shows a slip-lock 120 of the invention including a C-shaped slide 122, an L-shaped jaw 123, and two posts 124 and 125. The lower post 125 is threaded into the C-shaped slide, and the upper post 124 is threaded into a stud 126 that is integral with the C-shaped jaw. The stud loosely fits through a bore in the L-shaped jaw 123 which is retained by a collar 127 that is held against the stud when the upper post is threadably received by the stud. The slip-lock 120 becomes clamped to a rectangular rail whenever a force is applied to either of the posts 124 or 125 in any direction along a plane generally perpendicular to the post. The slip-lock of FIG. 8 is useful for retaining two retractors like the retractor 90 of FIG. 3, with the handle of one extending generally horizontal from the opening of a surgical wound and the other extending at an angle like that shown in FIG. 3.

EXAMPLE 1

Figure 4:
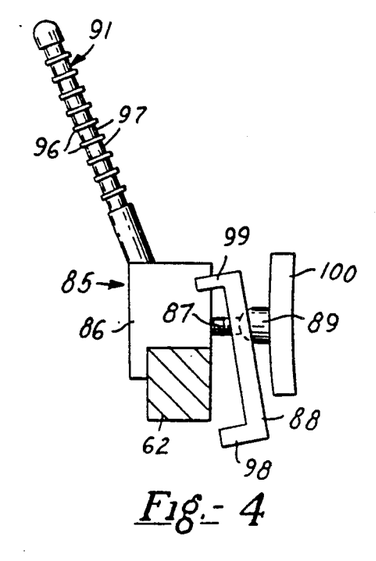
FIG. 4 is an enlarged elevation of a portion of the retraction device of FIG. 3 with its post in an unlocked position.

A prototype of the slip-lock 85 of FIGS. 3–5 has been made from stainless steel to the following dimensions: Another prototype slip-lock is identical to the slip-lock 85 except that its upstanding post extends perpendicularly to the under surface of the L-shaped slide 86. Both prototypes have been used with retractors having ratchet teeth as illustrated. Slip-locks have also been made as shown in FIG. 6 with a T-bar on the post for use with ordinary retractors that have toothless handles. Both systems have been used during many surgical operations, usually with the patient in the prone-kneeling position, but a number of cases have had transabdominal procedures, with the patient placed in a face-up, supine position, such as anterior spinal fusions. In every case, the slip-locks have performed without problem, holding the retractors firmly and without slipping and more stably than would be possible by hand. Surprisingly, both systems have made both placement and readjustment of the retractor blades much simpler than when retractors have been held by hand. The surgical assistants have praised the fact that they are freed from the strain of constantly pulling retractors and the consequent fatigue, and the assistants are better able to participate, observe and learn. The forces needed to pull the retractors can be considerible (e.g., 5 to 15 kg of force).

In the systems employing ratchet teeth, the manner in which the retractor is hooked to the post permits significant motion of the retractor blade, moving about the point of hooking, enough motion to permit some movement of the patient's body without dislodgement of retractor blade, an unexpected benefit of the novel system. Prior mechanical retractor holding systems have not permitted any significant motion of the blades, and even slight changes in the position of the patient have often dislodged the retractor blades and required them to be reset. This freedom of the blade to follow small positional changes permitted by the retraction device of this invention substantially replicates the reaction of an assistant who is holding a retractor by hand.

The security and ease of use of the both types of the novel retraction device (with and without ratchet teeth) has significantly improved on the accuracy and speed of certain surgical procedures, especially spinal fusions.

Although both types permit quick-changing of retractor blade positions, the placement of a blade at a particularly acute angle relative to the long axis of the surgical wound may require the use of a screw-lock (such as the bolt 87 of FIGS. 3–5) after the slip-lock has been employed to enhance the positioning or repositioning of the retractor or retractors.

We claim:

1. A slip-lock adapted for allowing the selective positioning of a surgical retractor at a surgical site relative to a support rail, which rail has a first side, a second side located opposite the first side, a third side located between the first and the second sides and a fourth side located opposite the third side and between the first and second sides, said slip-lock comprising:
   a slide having (a) a first surface that can be selectively positioned to contact the first side of the rail, and (b) a second surface that can be selectively positioned to contact the third side of the rail;
   a post fixed to the slide adapted to selectively engage the surgical retractor;
   a jaw;
   means for pivotally mounting said jaw to said slide so that the jaw can pivot with respect to said slide, adjacent the first side of the rail, wherein said pivotally mounting means includes a bore means defined in said jaw for loosely receiving said post;
   wherein said jaw has an end means located distally from the pivotally mounting means, for selectively lockingly engaging the fourth side of the rail when the jaw is pivoted into the rail when a force is placed on the post by the surgical retractor positioned at the surgical site.

2. A slip-lock adapted for allowing the selective positioning of a surgical retractor at a surgical site relative to a support rail, which rail has a first side, a second side located opposite the first side, a third side located between the first and the second sides and a fourth side located opposite the third side and between the first and second sides, said slip-lock comprising:
   a slide having (a) a first surface that can be selectively positioned to contact the first side of the rail, (b) a second surface that can be selectively positioned to contact the third side of the rail and (c) a third surface that can be selectively positioned to contact the second surface of the rail;
   a post fixed to the slide which can selectively engage the surgical retractor;
   a jaw;
   means for pivotally mounting said jaw to said slide so that the jaw can pivot with respect to said slide, adjacent the first side of the rail, wherein said pivotally mounting means includes a bore means defined in said jaw for loosely receiving said post; and
   wherein said jaw has an end means located distally from the pivotally mounting means, for selectively lockingly engaging the fourth side of the rail when the jaw is pivoted into the rail when a force is placed on the post by the surgical retractor positioned at the surgical site.

3. A slip-lock adapted to be slidably mounted on a rail for positioning a surgical retractor at a surgical site, which rail has a first side, a second side located opposite the first side, a third side located between the first and the second sides, and a fourth side located opposite the third side and between the first and second sides, said slip-lock comprising:

a slide having a first surface that can contact the first side of the rail, and said slide having a second surface that can contact the third side of the rail;
a first post fixed to the slide;
a jaw;
means for pivotally mounting said jaw to said slide;
wherein said slide has a C-shaped body and said jaw has an L-shaped body, said C-shaped body defining an arm, said post adapted to engage the retractor such that the post is repositioned when a force is applied to the retractor thus causing simultaneous pivoting of the jaw relative to the slide and the urging of the arm against the second side of the rail, in order to lock the jaw and slide about the rail.

4. The slip-lock of claim 3 wherein said first post has a T-shaped body adapted to allow a retractor to be frictionally secured to the T-shaped body.

5. The slip-lock of claim 3 including another post fixed to said slide and extending from the slide in a direction substantially opposite from the first post.

6. A surgical retraction device for placing tissue in traction at a surgical site, said surgical retraction device including:
a framework which includes a rail, which rail has:
(a) a first side;
(b) a second side located opposite the first side;
(c) a third side located between the first and the second sides; and
(d) a fourth side located opposite the third side and between the first and second sides;
a surgical retractor;
a slip-lock which is slidably mounted on said rail, said slip-lock has:
(a) a slide having a first surface that can contact the first side of the rail, and said slide having a second surface that can contact the third side of the rail;
(b) a post fixed to the slide which can engage the surgical retractor;
(c) a jaw;
(d) means for pivotally mounting said jaw to said slide;
(e) wherein the post is fixed substantially adjacent to the first surface of the slide and said pivotally mounting means includes a bore provided in the jaw, which post is loosely received through said bore; and
(f) wherein said slide has a C-shaped body and said jaw has an L-shaped body, said C-shaped body defining an arm, such that when said retractor is attached to said post a force applied to the retractor repositions the post simultaneously pivoting the jaw relative to the slide and urging the arm against the second side of the rail, in order to lock the jaw and slide about the rail.

7. A slip-lock adapted to be slidably mounted on a rail for positioning a surgical retractor at a surgical site, which rail has a first side, a second side located opposite the first side, a third side located between the first and the second sides and a fourth side located opposite the third side and between the first and second sides, said slip-lock comprising:
a slide having a first surface that can contact the first side of the rail, and said slide having a second surface that can contact the third side of the rail;
a post fixed to the slide;
a jaw;
means for pivotally mounting said jaw to said slide;
wherein said slide has an L-shaped body and said jaw has a C-shaped body, said C-shaped body defining an arm, said post adapted to engage the retractor such that the post is repositioned when a force is applied to the retractor thus causing simultaneous pivoting of the jaw relative to the slide and urging of the arm against the second side of the rail, in order to lock the jaw and slide about the rail; and
said pivotally mounting means includes a bifurcated arm of the C-shaped body that fits about and is pivotally mounted to said slide, and wherein said bifurcated arm includes means for limiting the rotation of the jaw relative to the slide;

8. The slip-lock of claim 7 including a bolt threadably received by the slide and a socket formed in the jaw for loosely receiving said bolt in order to restrict the pivotal movement of the jaw relative to the slide.

9. A slip-lock adapted to be slidably mounted on a rail for positioning a surgical retractor at a surgical site, which rail has a first side, a second side located opposite the first side, a third side located between the first and the second sides, and a fourth side located opposite the third side and between the first and second sides, said slip-lock comprising:
a slide having a first surface that can contact the first side of the rail, and said slide having a second surface that can contact the third side of the rail;
a post fixed to the slide;
a jaw;
means for pivotally mounting said jaw to said slide;
wherein the post is fixed substantially adjacent to the first surface of the slide; and wherein said pivotally mounting means includes a bore provided in the jaw, which post is received through said bore;
wherein said slide has a C-shaped body and said jaw has an L-shaped body, said C-shaped body defining an arm, said post adapted to engage the retractor such that the post is repositioned when a force is applied to the retractor thus causing simultaneous pivoting of the jaw relative to the slide and urging of the arm against the second side of the rail, in order to lock the jaw and slide about the rail.

* * * * *

UNITED STATES PATENT AND TRADEMARK OFFICE
CERTIFICATE OF CORRECTION

PATENT NO.   : 5,000,163

DATED        : March 19, 1991

INVENTOR(S)  : Charles D. Ray, et al.

It is certified that error appears in the above-identified patent and that said Letters Patent is hereby corrected as shown below:

Column 6, line 10, delete the numeral "88" and insert therefor --91--.

Column 7, line 27, after the word "dimensions", insert the following:

--C-shaped jaw 88

| | |
|---|---|
| distance between ends | 3.0 cm |
| distance from center of socket to nearest end | 0.9 cm | hemispherical ball 89

| | |
|---|---|
| diameter | 1.3 cm | upstanding post 91

| | |
|---|---|
| length | 7.5 cm |
| diameter of rings 96 | 0.6 cm |
| diameter of grooves 97 | 0.5 cm |
| spacing between rings | 0.3 cm-- |

Signed and Sealed this

Twenty-fifth Day of August, 1992

Attest:

DOUGLAS B. COMER

*Attesting Officer*   *Acting Commissioner of Patents and Trademarks*